(12) United States Patent
Kneifel et al.

(10) Patent No.: US 9,433,417 B2
(45) Date of Patent: Sep. 6, 2016

(54) DEVICE AND METHOD FOR APPLYING A MEDICAL LOCKABLE CLIP IN A TISSUE AREA

(75) Inventors: Bernhard Kneifel, Hagenbach (DE); Rainer Körber, Speyer (DE); Günter Herrmann, Grünstadt (DE); Klaus-Peter Brhel, Philippsburg (DE); Ekaterina Notheis, Glauburg (DE); Wolfgang Ries, Linkenheim (DE)

(73) Assignees: JOIMAX GMBH, Karlsruhe (DE); KARLSRUHER INSTITUT FÜR TECHNOLOGIE, Karlsruhe (DE)

( * ) Notice: Subject to any disclaimer, the term of this patent is extended or adjusted under 35 U.S.C. 154(b) by 1201 days.

(21) Appl. No.: 13/322,728

(22) PCT Filed: May 25, 2010

(86) PCT No.: PCT/EP2010/003166
§ 371 (c)(1),
(2), (4) Date: Nov. 28, 2011

(87) PCT Pub. No.: WO2010/136170
PCT Pub. Date: Dec. 2, 2010

(65) Prior Publication Data
US 2012/0071899 A1 Mar. 22, 2012

(30) Foreign Application Priority Data
May 26, 2009 (DE) .................. 10 2009 022 692

(51) Int. Cl.
*A61B 17/10* (2006.01)
*A61B 17/068* (2006.01)
(Continued)

(52) U.S. Cl.
CPC ....... *A61B 17/0682* (2013.01); *A61B 17/0644* (2013.01); *A61B 17/08* (2013.01);
(Continued)

(58) Field of Classification Search
CPC ............. A61B 17/0644; A61B 17/08; A61B 17/0682; A61B 17/10; A61B 17/105; A61B 17/083; A61B 17/081; A61B 17/1285; A61B 17/128; A61B 17/122
USPC ........................................ 91/417 A
See application file for complete search history.

(56) References Cited

U.S. PATENT DOCUMENTS 3,616,497 A * 11/1971 Esposito ..................... 24/542
4,317,451 A * 3/1982 Cerwin et al. ............. 606/220
(Continued)

FOREIGN PATENT DOCUMENTS

| DE | 19935904 C1 | 7/2001 |
| EP | 1 199 990 A1 | 5/2002 |
| EP | 1 199 990 B1 | 9/2004 |

*Primary Examiner* — Gregory Anderson
*Assistant Examiner* — Son Dang
(74) *Attorney, Agent, or Firm* — McGlew and Tuttle, P.C.

(57) ABSTRACT

A device and method are provided for clips or staples as an effective substitute for suture material when joining body tissue or covering body tissue with a mesh, such as is particularly used in fracture operations. The device for applying a medical lockable clip (1) in a tissue area, includes a) an automatic advancing mechanism oriented in the direction of the tissue area from a starting position and having a guide in the advancing direction for the clip, wherein the clip has two gripper teeth oriented in the advancing direction, b) a stop for the advancing mechanism, and c) a locking element displaceable with the advancing mechanism and having a locking mechanism on the clip side for locking the clip, wherein d) the locking element is displaceable together with and parallel to the advancing mechanism, and e) the stop does not limit the motion of the locking element.

14 Claims, 5 Drawing Sheets

(51) Int. Cl.
*A61B 17/064* (2006.01)
*A61B 17/08* (2006.01)
*A61B 17/00* (2006.01)

(52) U.S. Cl.
CPC ............ *A61B 17/10* (2013.01); *A61B 17/105* (2013.01); *A61B 2017/00539* (2013.01); *A61B 2017/00544* (2013.01)

(56) References Cited

U.S. PATENT DOCUMENTS

| | | | | |
|---|---|---|---|---|
| 4,325,376 | A * | 4/1982 | Klieman et al. | 606/143 |
| 4,349,028 | A * | 9/1982 | Green | 606/143 |
| 4,388,747 | A * | 6/1983 | Plummer | 24/535 |
| 4,424,929 | A * | 1/1984 | Weis | 227/32 |
| 4,485,952 | A * | 12/1984 | Weis | 227/7 |
| 4,514,885 | A * | 5/1985 | Delahousse et al. | 24/557 |
| 4,569,469 | A | 2/1986 | Mongeon et al. | |
| 4,763,390 | A * | 8/1988 | Rooz | 24/487 |
| 4,839,947 | A * | 6/1989 | Cohen et al. | 24/499 |
| 4,887,601 | A * | 12/1989 | Richards | 606/219 |
| 4,943,294 | A | 7/1990 | Knapp | |
| 4,983,176 | A * | 1/1991 | Cushman et al. | 606/151 |
| 5,047,047 | A * | 9/1991 | Yoon | 606/216 |
| 5,236,440 | A * | 8/1993 | Hlavacek | 606/219 |
| 5,258,007 | A * | 11/1993 | Spetzler et al. | 606/208 |
| 5,425,489 | A * | 6/1995 | Shichman et al. | 227/108 |
| 5,437,681 | A * | 8/1995 | Meade et al. | 606/145 |
| 5,464,413 | A * | 11/1995 | Siska et al. | 606/151 |
| 5,490,651 | A * | 2/1996 | Kump | 248/222.12 |
| 5,862,972 | A * | 1/1999 | Green et al. | 227/175.1 |
| 5,876,410 | A * | 3/1999 | Petillo | 606/142 |
| 6,010,513 | A * | 1/2000 | Tormala et al. | 606/142 |
| D426,767 | S * | 6/2000 | Meyers | D8/395 |
| 6,210,419 | B1 * | 4/2001 | Mayenberger et al. | 606/158 |
| 6,261,303 | B1 * | 7/2001 | Mayenberger et al. | 606/151 |
| 6,301,756 | B1 * | 10/2001 | Howard | 24/552 |
| 6,387,113 | B1 * | 5/2002 | Hawkins et al. | 606/219 |
| 6,461,364 | B1 * | 10/2002 | Ginn et al. | 606/142 |
| 6,793,663 | B2 | 9/2004 | Kneifel et al. | |
| 7,056,330 | B2 * | 6/2006 | Gayton | 606/219 |
| 7,264,625 | B1 * | 9/2007 | Buncke | 606/157 |
| 7,559,125 | B2 * | 7/2009 | Cofer | 24/487 |
| 7,740,159 | B2 * | 6/2010 | Shelton et al. | 227/176.1 |
| 7,875,029 | B1 * | 1/2011 | Hausen | 606/52 |
| 7,950,559 | B2 * | 5/2011 | Peterson et al. | 227/175.1 |
| 8,157,145 | B2 * | 4/2012 | Shelton et al. | 227/175.1 |
| 8,336,752 | B2 * | 12/2012 | Viola | 227/175.1 |
| 8,393,517 | B2 * | 3/2013 | Milo | 227/181.1 |
| 2002/0062130 | A1 * | 5/2002 | Jugenheimer et al. | 606/142 |
| 2002/0065535 | A1 | 5/2002 | Kneifel et al. | |
| 2004/0087987 | A1 * | 5/2004 | Rosenberg et al. | 606/157 |
| 2006/0079115 | A1 * | 4/2006 | Aranyi et al. | 439/395 |
| 2006/0151567 | A1 * | 7/2006 | Roy | 227/175.1 |
| 2006/0247643 | A1 | 11/2006 | Bhatnagar et al. | |
| 2007/0233187 | A1 * | 10/2007 | Lobello | 606/219 |
| 2008/0140089 | A1 * | 6/2008 | Kogiso et al. | 606/142 |
| 2008/0177300 | A1 * | 7/2008 | Mas et al. | 606/219 |
| 2009/0149870 | A1 * | 6/2009 | Jugenheimer et al. | 606/142 |
| 2011/0106148 | A1 * | 5/2011 | Ginn et al. | 606/213 |

* cited by examiner

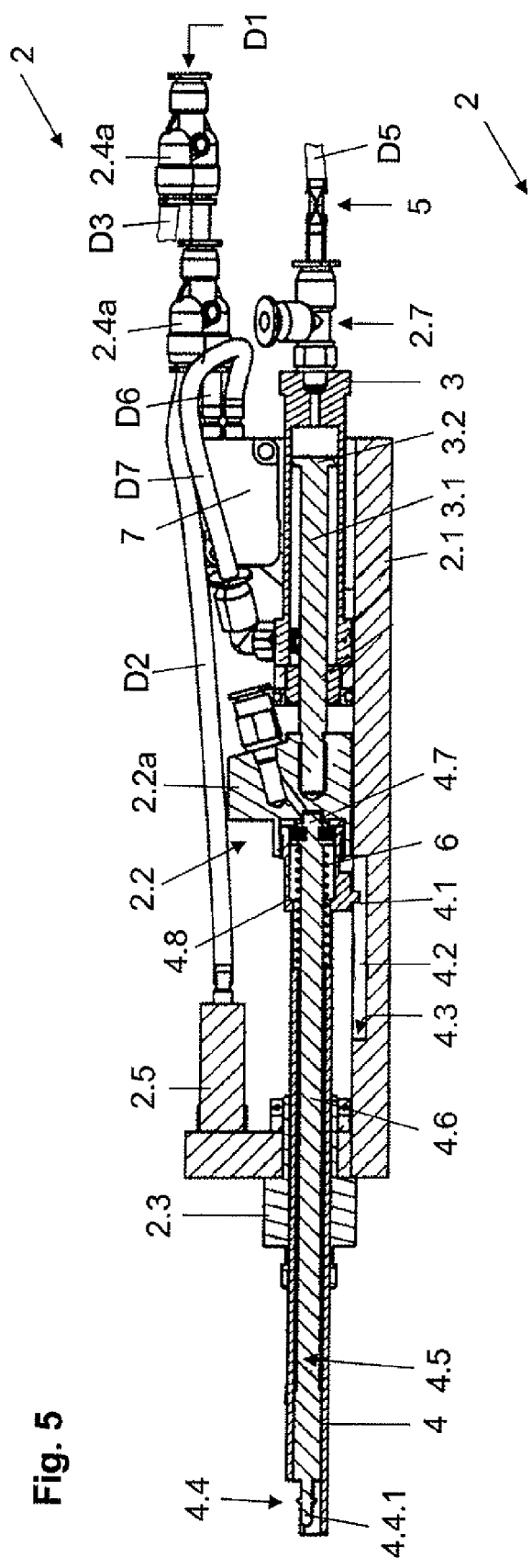
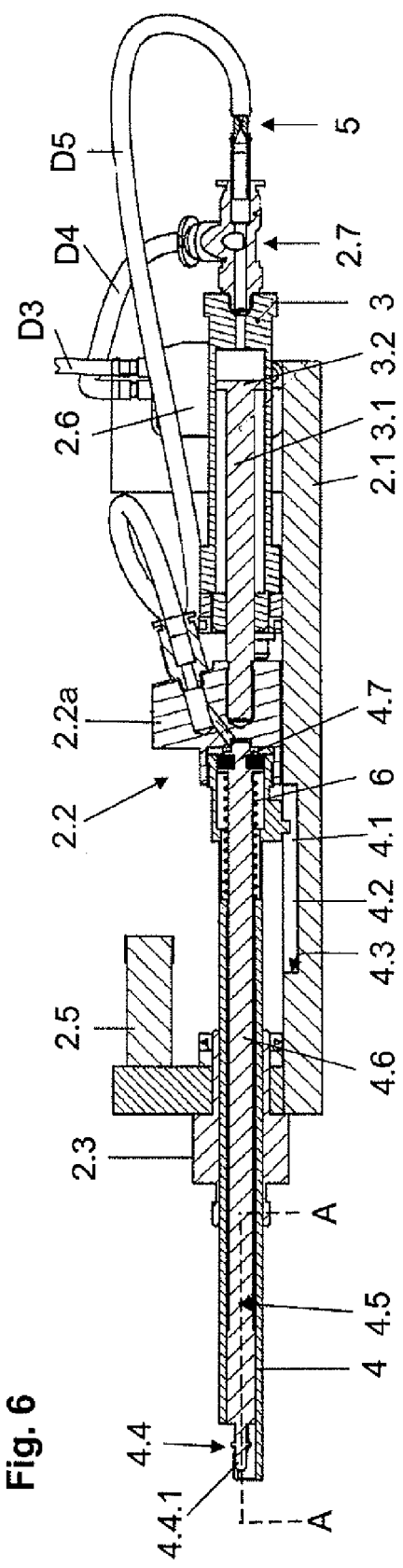
Fig. 5
Fig. 6

DEVICE AND METHOD FOR APPLYING A MEDICAL LOCKABLE CLIP IN A TISSUE AREA

CROSS REFERENCE TO RELATED APPLICATIONS

This application is a United States National Phase application of International Application PCT/EP2010/003166 and claims the benefit of priority under 35 U.S.C. §119 of German Patent Application DE 10 2009 022 692.3 filed May 26, 2009, the entire contents of which are incorporated herein by reference.

FIELD OF THE INVENTION

The present invention pertains to a device and a method for applying a medical lockable clip in a tissue area.

BACKGROUND OF THE INVENTION

Such a device is known from EP 1 199 990 B1. The drawback of the prior-art device is that the force for shooting in and closing the clip must be applied manually and the operation does not therefore lead to reliably reproducible, identical results; poor placement of the clip may at times occur as well.

SUMMARY OF THE INVENTION

A basic object of the present invention is therefore to provide a device and a method of the type mentioned in the introduction, which device and method make possible the reliable and reproducible placement of such clips in body tissues.

Said object is accomplished according to the present invention with a device for applying a medical lockable clip in a tissue area, which has the following features:
a) an automatic feed mechanism, which can be moved from a starting position in the direction of the tissue area, with a guide in the feed direction for the clip, wherein the clip has two gripping teeth directed in the direction of feed,
b) a stop for the feed mechanism as well as
c) a locking element movable with the feed mechanism with a clip-side locking mechanism for locking the clip, wherein
d) the locking element can be set into motion together with and in parallel to the feed mechanism, and
e) the stop does not limit the motion of the locking element.

To accomplish said object, the present invention also provides for a method for applying a medical lockable clip in a tissue area with the following steps:
a) Insertion of the clip into the guide of an automatic feed mechanism with the device, wherein the clip has two gripping teeth directed in the direction f feed,
b) automatic joint initiation of the feeding of the feed mechanism, of the locking element and of the clip in the direction of the tissue area up to a stop, which hinders a further feeding of the feed mechanism,
c) further selective automatic feeding of the locking element up to the clip, wherein this locking element triggers a clip-side locking mechanism for locking the clip.

An automatic device is a device that allows certain actions to take place independently and in a constrained manner after a triggering pulse. Accordingly, an automatic method is a method in which predetermined actions take place after a triggering pulse independently and in a constrained manner.

This may happen especially by means of a motor, wherein various types of motor drives, such as pneumatic, hydraulic, electric or even electromagnetic types, may be used.

It is achieved by the present invention that the clip can be shot into and closed in a certain tissue with equal force, so that equal, reproducible results can also be obtained. In addition, it becomes possible to use different shoot-in forces in tissues having different firmness or hardnesses in order to achieve reliable fixation of the clip even independently from the consistency of the tissue. In addition, both a higher shoot-in velocity and a stronger closing force can be applied through the present invention than it would be possible manually, as a result of which the fixation of the clip is likewise improved. The device may have a positive-locking or frictionally engaged mount for the clip, the locking element having a toggle lever element, which presses the gripping teeth of the clip against each other and releases the positive-locking and/or frictionally engaged mount of the clip. Provisions are made in a preferred embodiment for the mount to hold the clip preferably in a positive-locking manner by nubs, which mesh for locking the clip with corresponding nubs or depressions, which are formed in the clip mount, being provided laterally at the clip or the tooth flanks thereof. The positive-locking connection can be abolished by the change in the shape of the clip during the actuation of the toggle lever mechanism.

As an alternative, provisions are preferably made for the clip mount to hold the clip in a frictionally engaged manner in the clip mount itself or by a sliding press fit between a possible upper guide and a lower guide in the clip mount.

Provisions are made in preferred embodiments of the present invention for the feed mechanism to be formed by a shoot-in cylinder and for the locking element to be formed by a closing piston and/or to run in a cylinder liner of the shoot-in cylinder, in which the closing piston is sealingly guided.

In addition, provisions may be made in an alternative embodiment for the shoot-in cylinder and the closing cylinder to be connected via a T-shaped distributor and a pressure line, wherein a reducer is arranged in the pressure line leading to the closing cylinder, or they are connected by a spring, which is arranged between the feed mechanism and the locking element and which applies pressure on the latter components.

As a result, pressure is applied simultaneously and at equal value to both the shoot-in cylinder and the closing cylinder. The shoot-in cylinder is fed first up to the above-mentioned stop during the motion of the feed mechanism and it thus pushes the closing cylinder forward. The pressure admitted is admitted to the closing piston in a slowly increasing manner due to the reduced line cross-section of the reducer and to the length of the closing cylinder, which length is determined by the pressure line, and the locking element thus continues to be moved with a time offset, as a result of which the locking element acts on the toggle lever with a time difference from the feed mechanism.

It is reliably achieved as a result that the clip is first shot into the body tissue and it is then closed by the motion of the teeth towards one another.

Provisions are made in further preferred embodiments of the present invention for the locking element to have a guide for the clip as well as a restoring means for the pneumatic feed mechanism and the locking element for returning into the starting position, wherein the restoring means comprise especially pneumatic restoring pistons.

A manual valve actuation is followed according to the present invention by a pneumatically controlled triggering of the method according to the present invention. By contrast, the triggering mechanism is designed in a preferred embodiment as a device comprising an actuating valve, an auxiliary cylinder and an opening valve, wherein the compressed air feed is opened only after a predetermined opening pressure is reached. This guarantees that the method according to the present invention is always carried out with the same pressure and the same feed motion of the clip.

Provisions may preferably be made in an alternative embodiment of the pneumatic feed mechanism for the shoot-in piston within the shoot-in cylinder releasing a pressure connection from the wall of the shoot-in cylinder to the closing cylinder during the triggering after a certain feed path. Pressure is thus admitted to the closing piston and to the shoot-in piston with a time offset without a separate compressed air line and/or a T-distributor.

In addition, a clip magazine with a serial clip feed may be provided in the starting position. Provisions are preferably made by the present invention in this connection for a plurality of clips directed in the distal direction to be able to be inserted laterally from the closing piston, wherein said clips are arranged one after another. The clips can be preferably fed from the proximal end of a possible magazine by feed means, e.g., a spring, in the distal direction against a distal stop at the clip mount. After a clip has been applied, the closing piston is pulled back and the so is preferably the clip mount, and the clip in the magazine, which is closest to the distal stop at the clip mount, is pushed into the clip mount, e.g., by a leaf spring, and the next clip in the magazine is pushed against the distal stop.

Furthermore, the present invention provides for securing against unintended triggering of the automatic method.

Further advantages and features of the present invention appear from the claims and the following description, in which an exemplary embodiment of the present invention is explained in detail with reference to the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 5 is a schematic sectional view of the disposition of the device according to the present invention in the starting position and the feed mechanism in the standby position;

FIG. 6 is a schematic sectional view of the device according to the present invention according to FIG. 5 in a mutually opposite view thereto;

DESCRIPTION OF THE PREFERRED EMBODIMENTS

Figure 1:
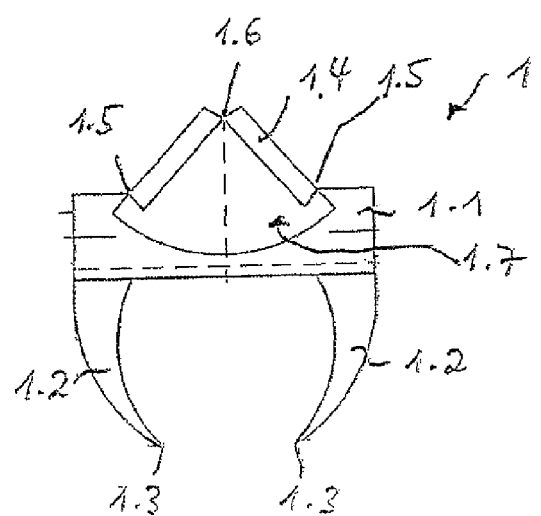
FIG. 1 is a view showing a clip in the starting configuration.

Referring to the drawings in particular, the resorbable clip used according to the present invention has centrally a deformable shoulder 1.1, on one side of which clip a tooth 1.2 each with a sharp tip 1.3 is formed at the end areas on one side of the clip.

On the side of the shoulder 1.1 located opposite the teeth 1.2, a toggle lever 1.4 is likewise formed in one piece, which is connected to the shoulder 1.1 via film hinges 1.5 and the two parts of which are likewise connected centrally to one another via a film hinge 1.6.

Under the toggle lever 1.4, the shoulder has a recess 1.7, into which the toggle lever 1.4 can be used in the overstretched position. The deformable shoulder 1.1, the toggle lever 1.4, the film hinges 1.5 and 1.6 and the recess 1.7 provide a clip-side locking mechanism.

Figure 2:
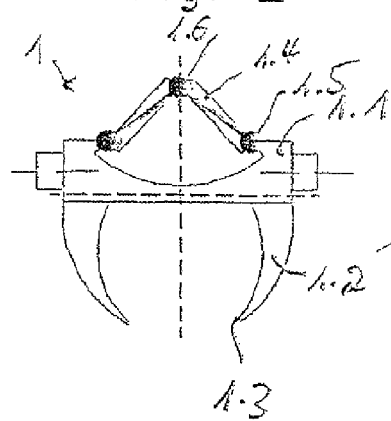
FIG. 2 is a view showing the clip in the same configuration with film hinges or joints indicated by dots.
Figure 3:
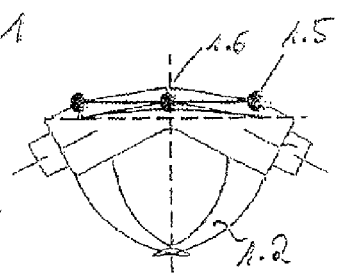
FIG. 3 is a view showing the clip with central axial application of pressure to the toggle lever immediately before the changeover into the stable end position.

FIGS. 1 and 2 show the clip 1 in the unloaded starting or standby position thereof with the teeth 1.3 opened. FIG. 3 shows a configuration of clip 1, in which a force is applied to said clip centrally at the two ends of the parts of the toggle lever 1.4, which said ends touch each other in the film hinge 1.6, whereas an opposite force acts on the ends of shoulder 1.1. As a result, the teeth 1.2 are closed, as this is shown in FIG. 3. Due to overstretching by means of the force acting corresponding to the configuration in FIG. 4, the toggle lever 1.4 reaches a stable position, in which it maintains the closing position of clip 1 even without further force actions on the middle area thereof.

Figure 4:
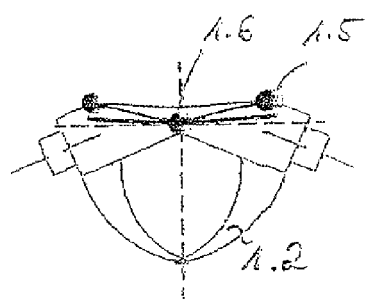
FIG. 4 is a view the clip in its stable end position with the toggle lever overstretched.

The device according to the present invention carries out the following steps one after another:

Feeding of the clip 1 into a starting or standby position according to FIGS. 1 and 2 while inserting the tips 1.3 of teeth 1.2 into a tissue; and subsequent closing of clip 1 or of the clamp corresponding to the configurations in FIGS. 3 and 4.

This will be explained in more detail below with reference to FIGS. 5 through 8.

FIG. 5 and FIG. 6 show vertical sections each through the device 2 according to the present invention, the two drawings showing mutually opposite views.

The device 2 according to the present invention has, at first, an essentially parallelepipedic housing 2.1 (shown only partially for clarity's sake), which has, on the one hand, a shooting unit 2.2, comprising a shoot-in cylinder 3 and a closing cylinder 4 with integrated safety means to prevent accidental triggering, and, on the other hand, a cylinder liner 2.3, with which the closing cylinder 4 is guided.

A shoot-in piston 3.1, which is screwed into the connection piece 2.2a of the shooting unit 2.2 by means of a thread, is arranged within the shoot-in cylinder 3. Furthermore, a closing cylinder 4, which is mounted in the cylinder liner 2.3 and is linearly movable together with the connection piece 2.2a, is connected to the connection piece 2.2a. Closing cylinder 4 is guided by means of a dog 4.1 in a groove 4.2 in housing 2.1. The feed motion of the shooting unit 2.2 is limited here by a stop 4.3 formed in the housing 2.1 for the dog 4.1.

At its front end, closing cylinder 4 has a clip mount 4.4, in which the clip 1 is held, especially in a positive-locking and angularly aligned as well as positioned manner. As is shown in FIG. 5, clip 1 can lie on the clip mount 4.4, which protrudes as an extension 4.4.1 beyond the distal end of the closing piston 4.5, while it is being held in a positive-locking manner. For the positive-locking connection of clip 1, the latter may have nubs (not shown) on its tong flanks 1.8, which nubs can be locked or inserted in a positive-locking manner into corresponding nubs or depressions (not shown), which are arranged on the support surface of the clip mount 4.4.

Figure 7:
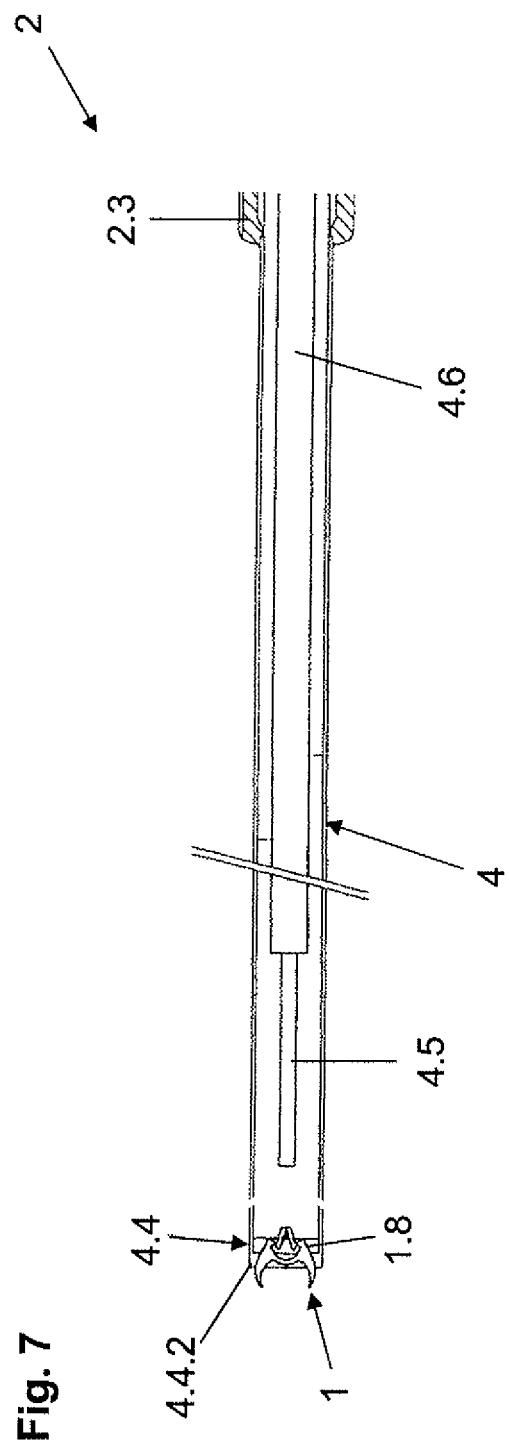
FIG. 7 is a schematic view of the distal end of the device according to an alternative embodiment with clip inserted along section A-A in FIG. 6.
Figure 8:
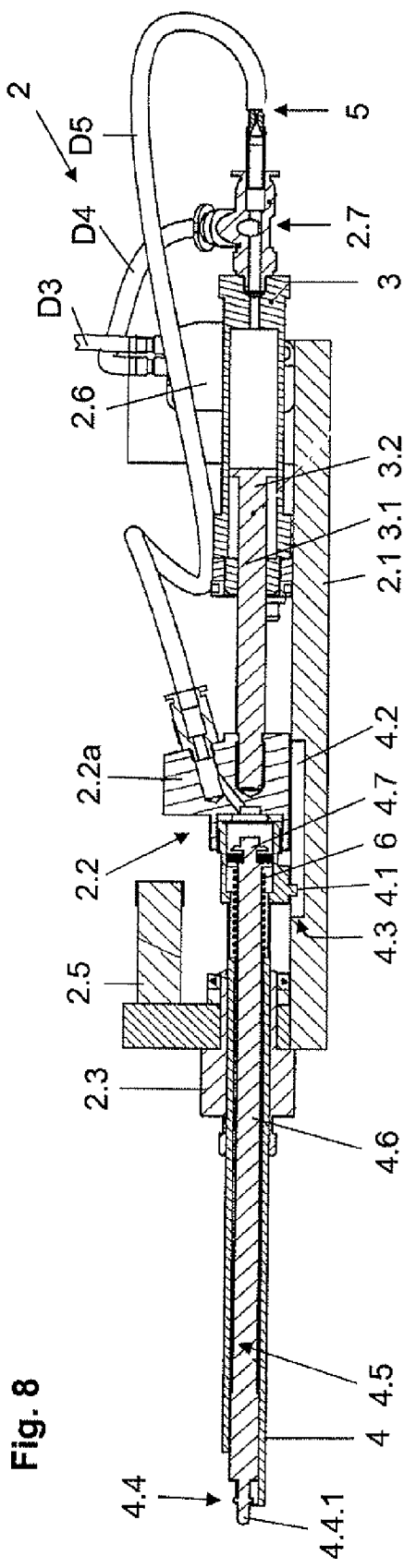
FIG. 8 is another schematic sectional view of the device according to FIG. 5 with a partially fed feed mechanism.
Figure 9:
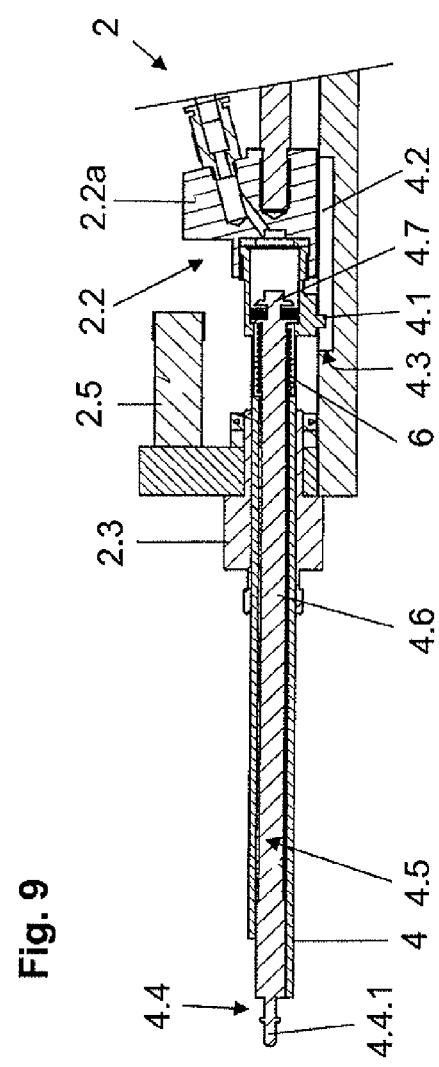
FIG. 9 is a schematic partial sectional view of the front area of the device according to the present invention according to FIG. 5 with the locking element (closing piston) fed.

The clip is preferably also held laterally, as is also shown in the further embodiment in FIG. 7, which schematically shows a section through the front area of the clip mount 4.4 according to an alternative embodiment corresponding to section A-A in FIG. 6. FIG. 7 shows an alternative embodiment of the clip mount 4.4 at the distal end of the closing cylinder 4. Clip 1 is not placed or inserted here onto an extension 4.4.1 of a closing piston 4.5 arranged within the closing cylinder 4 but it can be placed or inserted into a tong-like end area 4.4.2 of the closing cylinder 4.

A closing piston 4.5, which has a piston rod 4.6, which can act through the closing cylinder 4 onto the middle area of the toggle lever 1.4 of the clip 1 and can thus apply the closing force mentioned with reference to FIGS. 1 through 4 for the clip 1, is arranged within the closing cylinder 4. An O-ring seal is recessed in the rear area of the closing piston 4.5 in a piston head 4.7, with which the closing piston 4.5 is guided sealingly within the closing cylinder.

A coil spring 6, which holds with a certain force the closing piston 4.1 in its position shown in FIG. 1, in which it is retracted from the clip, is arranged under the piston head 4.7.

Furthermore, housing 2.1 has a restoring means for the shooting unit 2.2. A restoring valve 7 (shown in FIG. 5) has a manual rotary knob (not shown), wherein a compressed air line D6 is connected to the compressed air supply D1 and a compressed air line D7 leads from the restoring valve 7 into the front part of the shoot-in cylinder 3 in front of the shoot-in piston head 3.2.

Compressed air is correspondingly available permanently from the compressed air supply D1 at the triggering valve 2.2 (via D2), at the opening valve 2.6 (via D3) and at the restoring valve 7.

The compressed air supply D1 leads via an inlet and two Y-shaped distributors 2.4a, 2.4b arranged downstream one after another as well as via a pressure line D2 to a triggering valve 2.5. Triggering valve 2.5 has a manually actuatable rotary knob (not shown) and is connected via another pressure line to an auxiliary cylinder (both likewise not shown in FIG. 5; see FIG. 10), which is used to actuate another compressed air valve, an opening valve 2.6 (FIG. 6). The compressed air supply D1 is connected on the inlet side to the opening valve 2.6 (FIGS. 5, 6, 10) by means of a pressure line D3. Another pressure line D4 connects hereafter the opening valve 2.6 on the outlet side to a T-shaped distributor 2.7, one outlet of which is arranged directly at the rear end of a shoot-in cylinder 3. A reducer, which is used to reduce the pressure in a connected pressure line D5, which connects the reducer 5 to an inlet in the connection piece 2.2a of the shooting unit 2.2, is arranged at a second outlet.

If the triggering valve 2.5 is opened, the compressed air is sent to the above-mentioned auxiliary cylinder, not shown (cf. auxiliary cylinder 8 in FIG. 10), which will then bring about opening of the opening valve 2.6. It is thus guaranteed that the admission of pressure to the entire system remains the same during both rapid actuation of the pushbutton and slower actuation of the manual pushbutton, because the auxiliary cylinder releases the compressed air passage only beginning from a certain settable pressure only. The compressed air flows through the opening valve 2.6 via the pressure line D4 to a T-shaped distributor 2.7, from which the compressed air is sent in two mutually opposite directions. The side of the T-shaped distributor 2.7, which is attached directly to the shoot-in cylinder 3, carries compressed air with full pressure admission directly to the shoot-in piston 3.1 running in the shoot-in cylinder 3 and thus pushes the entire shooting unit 2.2 forward. The closing cylinder 4 is now pushed through the cylinder liner 2.3. The motion takes place up to a stop 4.3, and dog 4.1 is guided by the groove 4.2. As a result, the clip 1 is moved out of the housing 2.1 and when the housing with its front end comes to lie on body tissue, optionally via the intermediate of a net, the teeth 1.2 of clip 1 are shot into the tissue.

Simultaneously with the application of pressure of the shoot-in cylinder 3, the compressed air is sent through a pressure reducer 5 arranged on a side of the distributor 2.7 opposite the shoot-in cylinder 3 through this reducer 5 and a pressure line D5 connected to same through the transition piece 2.2a of the shooting unit 2.2 into the closing cylinder 4 behind the piston head 4.7 of the closing piston 4.5. The closing piston 4.5 is thus fed through the closing cylinder 4 in a time-delayed manner by a time difference t and shoots with considerable force against the center of the toggle lever 1.4, as a result of which the closing force described with reference especially to FIGS. 3 and 4 is exerted on same, the clip 1 is closed while moving the teeth 1.3 against one another, and finally, the toggle lever is brought into its overstretched stable closing position (shown in FIG. 4), in which it is held in the tissue, as a result of which a net that may have thus possibly also been interposed is attached to the tissue. The device 2 of the toggle lever 1.4 can then be removed from the clip 1 in this closed position of the lever. The certain time difference t is determined here mainly by the reducer 5 and the length of the pressure line D5 to the connection piece 2.2a of the shooting unit 2.2.

Restoration of the closing piston 4.5 and of the piston head 4.7 is guaranteed by a coil spring 5, whose prestress pushes back the closing piston 4.5 with a certain weak force into the starting position thereof, which is shown in FIG. 5. In the view shown in FIG. 8, the clip is already inserted into the tissue and pneumatic restoration of the shoot-in cylinder 3 and hence of the complete shooting unit 2.2 takes place. Compressed air is sent by manually actuating a rotary knob at a restoring valve 7 and the compressed air supply D1 via the compressed air lines D6 and D7 within the shoot-in cylinder 3 to the area in front of the piston head 3.2 of the shoot-in piston 3.1, by means of which the shoot-in piston 3.1 is moved again back in the rearward direction into its starting position (cf. FIG. 5). The reverse motion of the shoot-in piston 3.1 is limited in the rearward direction by the dimensions of the shoot-in cylinder 3.

Figure 10:
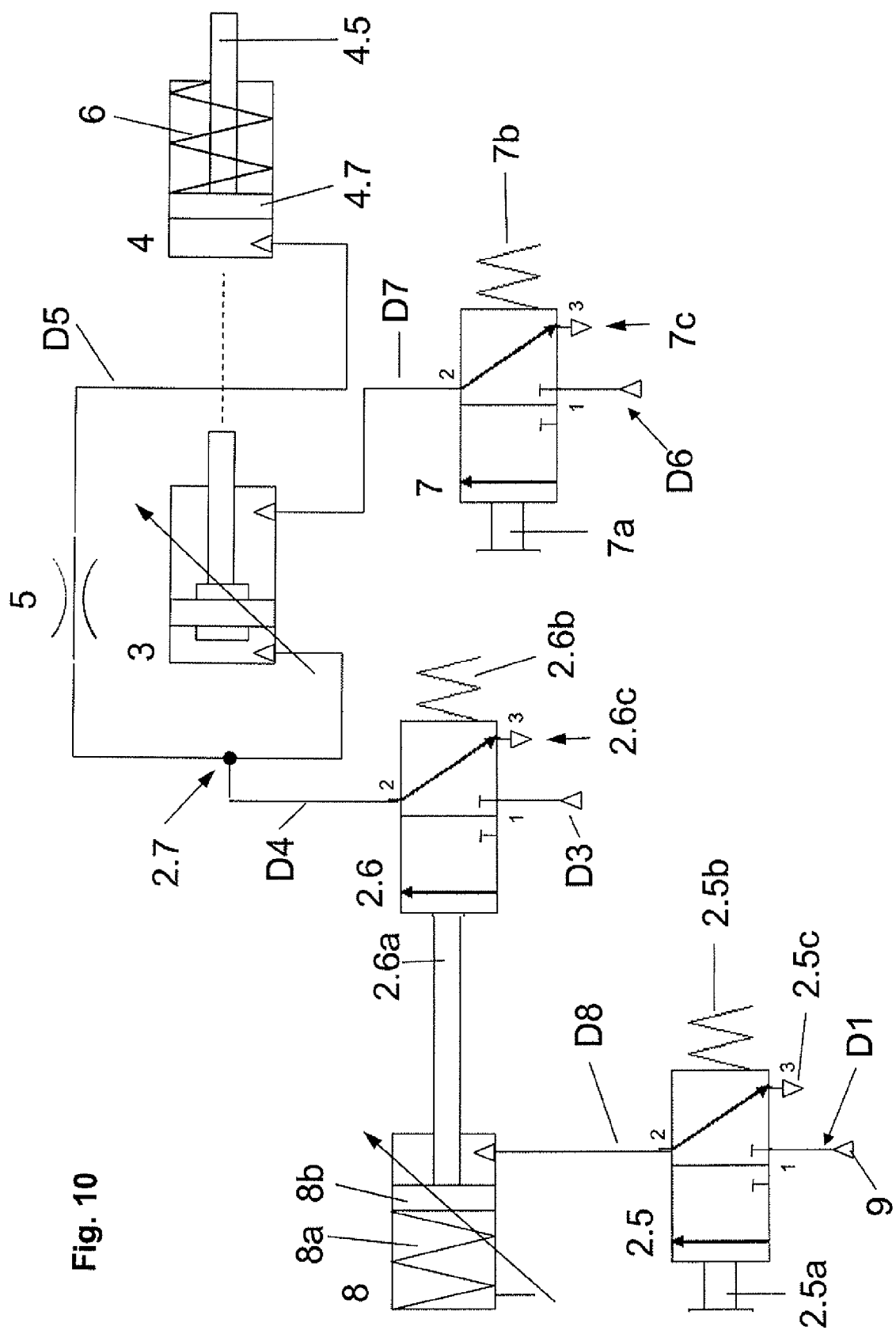
FIG. 10 is a pneumatic diagram according to DIN/ISO 1219 of an expanded embodiment of the device according to the present invention.

FIG. 10 shows a pneumatic circuit diagram of an expanded embodiment of the device according to the present invention according to DIN/ISO 1219 and it schematically describes the route of the compressed air through the device according to the present invention. The pneumatic circuit diagram contains pneumatic circuit symbols, which are assigned to the individual components of the device according to the present invention corresponding to FIGS. 5 through 9 and whose meanings will be explained in more detail below. The pneumatic circuit symbols show the valves in their rest positions, i.e., the state which the valves assume in an unactuated state.

The sequence of the pneumatic circuit diagram is as follows:

Compressed air is sent from a triggering valve 2.5 via an auxiliary cylinder 8 to an opening valve 2.6;

compressed air is sent into the shoot-in cylinder 3 via a T-shaped distributor 2.7, which represents the transition of feeding of the entire shoot-in cylinder 3 to the feed of the closing piston 4.5 in FIG. 6;

compressed air continues to be sent through the reducer 5 to the closing piston 4; and the shoot-in cylinder 3 is moved into its starting position by manual actuation of the rotary knob by means of the restoring valve 7.

The direction of the compressed air is described in the pneumatic circuit diagram by a triangle 9 directed in the direction of the compressed air flow, and thus it shows that the compressed air flow is sent, starting from the compressed air supply D1, from the triggering valve 2.5 to the auxiliary cylinder 8. The first circuit symbol in the pneumatic method in FIG. 10 is the triggering valve 2.5 according to FIGS. 5 through 8 and is a 3/2-way valve with a valve plunger 2.5*a* and a restoring spring 2.5*b*. It is opened against the restoring spring 2.5*b* by actuation by muscle strength, closed by the restoring spring 2.5*b* and vented by means of a vent hole 2.5*c*.

Valve 2.5 is followed by the auxiliary cylinder 8, which is a single-acting cylinder with a piston-side, adjustable restoring spring 8*a* and with a cylinder piston 8*b*, wherein an arrow through the valve designates the adjustability of restoring spring 8*a*. The compressed air line D8 sends compressed air from valve 2.5 into the front, spring-loaded area of the auxiliary cylinder 8. Spring 8*a* is compressed by means of the compressed air against its action by the cylinder piston 8*b*. When a predefined opening pressure, which is preset by setting the spring rate of spring 8*a*, is exceeded, spring 8*a* triggers the auxiliary cylinder 8 and brings the cylinder piston 8*b* back into the starting position thereof. Cylinder piston 8*b* is connected to a valve plunger 2.6*a* of the opening valve 2.6 and thus actuates the opening valve 2.6 when returning into its starting position. This is another 3/2-way valve with a restoring spring 2.6*b* and a vent hole 2.6*c*, which valve is triggered by the auxiliary cylinder 8 via the manually actuatable valve plunger 2.5*a*.

Auxiliary cylinder 8 and opening valve 2.6 act as a closing accelerator. It shall be guaranteed that the same pressure can flow through the lines with each use of the method according to the present invention, the shoot-in piston 3.1 is always fed with the same pneumatic force and thus it always presses the clip into the tissue with the same acceleration and force. The variable actuation by the user's muscle strength is thus compensated, because he does not trigger the valve with the same strength during each use of the device according to the present invention.

A T-shaped distributor 2.7 branches off a pressure line D4 coming from the opening valve 2.6. Compressed air is sent, on the one hand, to the shoot-in cylinder 3, which is a double-acting cylinder with damping adjustable on both sides. On the other hand, compressed air is sent through a reducer 5 by means of a pressure line D5 into the rear part of the closing cylinder 4. Shoot-in cylinder 3 is a cylinder with a damping adjustable on both sides, which cylinder can thus be moved in two directions.

An arrow through the circuit symbol of the shoot-in cylinder 3 indicates the adjustability of the cylinder, because the cylinder can be operated with different pressures. Compressed air enters the rear part of the shoot-in cylinder from the distributor 2.7 and brings about the feed thereof (cf. FIG. 7). Lying on the same axis (indicated by a broken line), the closing piston 4.5 follows with a restoring spring 6 on one side. Compressed air likewise enters here the rear part of the closing piston 4.5 after a certain time delay, which is determined by the passage through the reducer, the length of the compressed air line leading to the closing piston 4.5 and the valve of the compressed air, and pushes said closing piston forward with increasing pressure against the action of spring 6, as this is shown in FIGS. 5 through 8. After placing the clip 1, the closing piston 4.5 is restored via the restoring spring 6 thereof during the release of the pressure in the pressure lines located in from thereof by venting the valves 2.5 and 2.6. The 3/2-way valves 2.5 and 2.6 have a second valve position for this, which makes possible the venting of the pressure lines via the vent holes 2.5*c* and 2.6*c*.

The pneumatic restoring means of the shoot-in cylinder 3 is designated by the restoring valve 7, a 3/2-way valve with restoring spring 7*a* and with a vent hole 7*b*, which valve is actuated by muscle strength by means of valve plunger 7*c*. The compressed air is sent through the valve 7 via the compressed air line D7 into the front part of the shoot-in cylinder 3 and it thus pushes the shoot-in piston 3.1 back again into its starting position (cf. description for FIGS. 5 through 8). The restoring valve itself is brought again into its starting position by a restoring spring 7*a*. The outgoing air pressure is released from the restoring mechanism including the shoot-in cylinder 3 by means of the second possible valve position of the compressed air restoring valve 7 via vent hole 7*b*.

It appears from the above that as soon as an operator—a physician—moves the triggering valve 2.5 into an open position, the further method takes place automatically under the action of the compressed air released, namely in three steps, by the clip 1 being first moved by the shoot-in cylinder 3 out of the housing 2.1 of the device 2 and being shot into the tissue. After blocking of the shoot-in cylinder 3, the clip 1 is closed in a second step by the stop 2.9 under the action of the inner closing piston 4 on the toggle levers 1.4 and is thus fixed to the tissue. As a last step, the shoot-in piston is moved again into the starting position by actuating the restoring valve 6 and limiting the rearward motion by the rear wall of the shoot-in cylinder 3.

Instead of an automatic pneumatic action method, as it was brought about on the basis of the triggering pulse brought about by the actuation of the compressed air valve, an automatic hydraulic or electrically or even electromagnetically controlled method may take place as well, for example, by means of an electric motor drive or even a sealed action on electromagnets, which move first the shoot-in cylinder 3 and then the closing piston 4.5 of the housing 2.1 of device 2 in the forward direction (left in the drawings).

The invention claimed is:

1. A device for the application of a medical lockable clip in a tissue area, the device comprising:
    an automatic feed mechanism, which can be moved from a starting position in the direction of the tissue area, with a guide in a feed direction for the clip;
    a stop for the automatic feed mechanism;
    a locking element, which can be moved with the automatic feed mechanism; and
    a locking mechanism, wherein:
    the locking element is set into motion together with and in parallel to the automatic feed mechanism;

the automatic feed mechanism is formed by a shoot-in cylinder with a shoot-in piston and the locking element is formed by a closing cylinder with a closing piston;

the shoot-in cylinder and the closing cylinder are connected via a T-shaped distributor and a pressure line wherein a reducer is arranged in the pressure line leading to the closing cylinder; and the stop does not limit the motion of the locking element.

2. The device in accordance with claim 1, wherein the guide has a positive-locking and/or frictionally engaged mount for the clip.

3. The device in accordance with claim 1, wherein the locking mechanism has a toggle lever element.

4. The device in accordance with claim 1, further comprising a triggering mechanism comprising a triggering valve, an auxiliary cylinder and an opening valve.

5. The device in accordance with claim 4, wherein an air supply to the automatic feed mechanism can be pneumatically released by means of the triggering valve, the auxiliary cylinder and the opening valve only after a preset opening pressure has been reached.

6. The device in accordance with claim 4, wherein said triggering valve and said opening valve have vent holes to release pressure in pressure lines of the triggering valve and the opening valve.

7. The device in accordance with claim 1, further comprising a restoring means for moving the automatic feed mechanism and the locking element into their respective starting position.

8. The device in accordance with claim 7, wherein the restoring means comprises pneumatic restoring pistons.

9. The device in accordance with claim 7, further comprising a spring arranged between the automatic feed mechanism and the locking element and acting on the latter.

10. The device in accordance with claim 1, wherein the closing cylinder, within which the closing piston guides, runs in a cylinder liner.

11. The device in accordance with claim 1, further comprising a clip magazine with a serial clip feed in the starting position.

12. The device in accordance with claim 1, wherein the automatic feed mechanism is a pneumatic or hydraulic feed mechanism.

13. A device for the application of a medical lockable clip in a tissue area, the device comprising:

an automatic feed mechanism, which can be moved from a starting position in the direction of the tissue area, with a guide in the feed direction for the clip;

a stop for the automatic feed mechanism;

a locking element, which can be moved with the automatic feed mechanism;

a triggering mechanism comprising a triggering valve, an auxiliary cylinder and an opening valve; and a locking mechanism, wherein:

the locking element is set into motion together with and in parallel to the automatic feed mechanism;

said triggering valve and said opening valve have vent holes to release a pressure in pressure lines of said triggering valve and said opening valve; and the stop does not limit the motion of the locking element.

14. A system, comprising:

a device for the application of a medical lockable clip having two gripping teeth directed in a feed direction in a tissue area, the device comprising:

an automatic feed mechanism, which can be moved from a starting position in the direction of the tissue area, with a guide in a feed direction for the clip;

a stop for the automatic feed mechanism;

a locking element, which can be moved with the automatic feed mechanism; and a locking mechanism, wherein:

the locking element is set into motion together with and in parallel to the automatic feed mechanism;

the automatic feed mechanism is formed by a shoot-in cylinder with a shoot-in piston and the locking element is formed by a closing cylinder with a closing piston;

the shoot-in cylinder and the closing cylinder are connected via a T-shaped distributor and a pressure line wherein a reducer is arranged in the pressure line leading to the closing cylinder; and the stop does not limit the motion of the locking element.

* * * * *